United States Patent [19]

Saint-Remy et al.

[11] Patent Number: 5,543,145
[45] Date of Patent: Aug. 6, 1996

US005543145A

[54] PHARMACEUTICAL COMPOSITION AND METHOD FOR THE SUPPRESSION OF FACTOR VIII INHIBITOR PRODUCTION

[75] Inventors: Jean-Marie Saint-Remy, Grez-Doiceau; Philippe Lebrun, Namur; Serge Lebeque; Pierre L. Masson, both of Brussels, all of Belgium; Henry S. Kingdon, Pasadena, Calif.

[73] Assignees: Baxter International, Inc., Chicago, Ill.; International Institute of Cellular and Molecular Pathology, Brussels, Belgium

[21] Appl. No.: 278,974

[22] Filed: Jul. 21, 1994

Related U.S. Application Data

[63] Continuation of Ser. No. 844,928, Mar. 4, 1992, abandoned, which is a continuation of Ser. No. 255,350, Oct. 11, 1988, abandoned, which is a continuation-in-part of Ser. No. 38,985, Apr. 16, 1987, abandoned, which is a continuation-in-part of Ser. No. 651,073, Sep. 17, 1984, Pat. No. 4,740,371.

[51] Int. Cl.⁶ ................................................ A61K 39/395
[52] U.S. Cl. ........................................ 424/133.1; 424/130.1
[58] Field of Search .............................. 514/12; 436/518; 424/10, 85.8, 133.1, 130.1

[56] References Cited

U.S. PATENT DOCUMENTS

| | | | |
|---|---|---|---|
| 4,140,679 | 2/1979 | Malley | 424/88 |
| 4,234,569 | 11/1980 | Marsh | 424/91 |
| 4,344,938 | 8/1982 | Sedlacek et al. | 260/112 B |
| 4,545,986 | 10/1985 | Malley | 424/91 |
| 4,564,600 | 1/1986 | Ali et al. | 436/513 |
| 4,649,132 | 3/1987 | Zimmerman | 514/12 |
| 4,670,543 | 6/1987 | Bourgois et al. | 530/383 |
| 4,714,759 | 12/1987 | Whitaker | 530/391 |

FOREIGN PATENT DOCUMENTS

| | | |
|---|---|---|
| 0217577 | 4/1987 | European Pat. Off. . |
| 0253455 | 1/1988 | European Pat. Off. . |
| 0209229 | 12/1982 | Japan . |
| 87938 | 11/1985 | Romania . |

OTHER PUBLICATIONS

Lazarchick et al., *J. Clin. Invest.*, 60 (1977), pp. 1070–1079.
Kasper, *Factor VIII Inhibitors*, edited by Hoyer, published by A. R. Liss, Inc., New York, N.Y. (1984), pp. 87–98.
Foster et al., *J. Clin. Investigation*, 82, (1988), pp. 123–128.
Fulcher et al., *Blood*, 69, No. 5 (1987), pp. 1475–1480.
Shima et al., *Brit. J. Hematol.*, 70, (1988), pp. 63–69.
Rotblat et al., *Biochemistry*, 24 (1985), pp. 4294–4300.
Allain et al., *Thrombos. Hemostas.*, 45, No. 3 (1981), pp. 285–289.
Lazarchick et al., *Annals of Clinical and Laboratory Science*, 16, No. 6 (1986), pp. 497–501.
Lazarchick and Hoyer, *J. Clin. Invest.*, 62, (1978), pp. 1048–1052.

Nilsson et al., *The New England J. of Medicine*, 318 (1988) pp. 947.
Nilsson et al., *Thromb. & Hematol.*, 58 No. 1 (1987), p. 519.
Goodall et al., *Thrombosis & Hematol.*, 54 No. 4 (1985), pp. 878–891.
de la Fuente et al., *Blood*, 64, No. 3 (1984), pp. 672–678.
Moffatt et al., *Brit. J. of Hematol.*, 71 (1989), pp. 85–90.
Tiarks et al., *Thrombosis Research*, 45 (1987) pp. 527–537.
Sultan et al., *The Lancet*, (Oct. 6, 1984), pp. 765–768.
Barkas et al., *J. Clin. Lab. Immunol.*, 7 (1982), pp. 223–227.
Borel et al., *Annals New York Academy of Sciences*, (1986) pp. 296–305.
Caulfield et al., *J. Immunol.*, 138, No. 11 (1987), pp. 3680–3683.
Allain, *Scand. J. Hematol.*, 33, suppl. 40 (1984), pp. 177–179.
"Suppression of Reaginic Antibody Formation, IV, Suppression of Reaginic Antibodies to Penicillin in the Mouse", Weng Y. Lee et al., *The Journal of Immunology*, vol. 117, No. 3, Sep. 1976, pp. 927–934.
"Tolerization of $B_\epsilon$ Cells by Conjugates of Haptens and Isologous $\gamma$-Globulins", Weng Y. Lee et al., *Cellular Immunology* 58, 385–397 (1981).
"'ALERGIM', A Specific Immune Complex for the Intraseasonal Treatment of Pollinosis. A Clinical Trial", E. G. Seropian et al., *Abstracts Interlaken 1984—6th European Immunology Meeting*, p. 325 (1984).
"Alergim$^R$—A New Antiallergic Product Which Down-Regulates B Lymphocyte Functions", G. Szegli et al., Arch. Roum. Path. Exp. Microbiol., T. 46, No. 1, pp. 73–82, Jan.–Mar. 1987.
"Regulatory Effect of Antibody on the Immune Response", Jonathan W. Uhr et al., *Advances in Immunology* vol. 8, pp. 81–127, 1968.
Bernstein, I. L., et al., "Immunoregulatory Function of Specific IgG", *Int. Archs. Allergy Appl. Immun.*, 58: 30–37 (1979).
E. Seropian et al., "'Alergim'—Blocking Antibody IgG Specific in Intraseasonal Treatments of Pollenosis: Clinical Results", *Imunologie XIII*, Academia De Stiinte Medicale Comisia Nationala De Imunologie Subcomisia Tirgu Mures 1984.
Andrew F. Geczy, et al, "Suppression of Reaginic Antibody Formation in Guinea Pigs by Anti–idiotypic Antibodies," *J. Allergy Clin Immunol*, vol. 62(5): 261–270, 1978.

(List continued on next page.)

*Primary Examiner*—Raymond Henley, III
*Attorney, Agent, or Firm*—Lane, Aitken & McCann

[57] ABSTRACT

A pharmaceutical composition suitable for administration to human beings for suppressing the production of factor VIII inhibitor includes:

an immune complex of factor VIII antigen component and factor VIII inhibitor component, the components being present in a ratio such that the inhibitor blocks essentially all relevant binding sites of the antigen; and a pharmacologically acceptable carrier or diluent. The invention also provides a method of administering the compositions to suppress the production of inhibitor to factor VIII.

26 Claims, No Drawings

OTHER PUBLICATIONS

G. G. B. Klaus, "Antigen–antibody Complexes Elicit Anti-–Idiotypic Antibodies to Self–Idiotopes," *Nature,* vol. 272, pp. 265–266, Mar. 16, 1978.

Kurt Blaser, et al, "Suppression of Phoshorylcholine–Specific IgE Antibody Formation in BALB/c Mice by Isologous Anti–T 15 Antiserum," Eur. J. Immunol. 1979.9:1017–1020.

Kurt Blaser, et al, "Suppression of the Benzylpenicilloyl–(BPO) Specific IgE Formation With Isologous Anti-–Idiotypic Anti–bodies in BALB/c Mice," *The Journal of Immunology,* vol. 125, No. 1, pp. 24–30, Jul., 1980.

K. Blaser, et al, "Investigation of a Syngeneic Murine Model for the Study of IgE Antibody Regulation With Isologous, Antiidiotypic Antibodies," *Int. Archs Allergy Appl. Immun.* 64: 42–50 (1981).

Raif S. Geha, M.D., "Current Concepts in Immunology," *The New England Journal of Medicine,* vol. 305, No. 1, pp. 25–28, Jul. 2, 1981.

A. I. Farkas, et al, "Immunogenicity of Antigen Complex With Antibody," *Immunology,* vol. 45, pp. 483–492, 1982.

Raif S. Geha & Marc Comunale, "Regulation of Immunoglobulin E Antibody Synthesis in Man by Antiidiotyic Antibodies," *J. Clin. Invest.,* vol. 71, pp. 46–54, Jan., 1983.

Paul D. Buisseret, "Allergy," *Scientific American,* pp. 82–91, Aug., 1982.

Howard J. Sanders, "Allergy, A Protective Mechanism Out of Control," *Chemical & Engineering News,* vol. 48, pp. 84–135, May 11, 1970.

"Primer on Allergic and Immunologic Diseases," *Journal of the American Medical Association,* vol. 248, No. 20, Nov. 26, 1982.

E. P. Hall et al., "Regulation of rat IgE responses by immune complexes", *Immunology,* vol. 61 (1987), pp. 415–419.

Arend et al, "In Vitro Adherence of Soluble Immune Complexes to Macrophages", 136 J. Exp. Med. 514 (1972).

Klaus, "Cooperation Between Antigen–Reactive T Cells and Anti–Idiotypic B Cells in the Anti–Idiotypic Response . . . " 278 Nature 354 (Mar. 22, 1979).

Klaus, "Generation of Memory Cells, III. Antibody Class Requirements for the Generation of B–Memory Cells by Antigen–Antibody . . . " 37 Immunology 345 (1979).

Caulfield et al, "Induction of Idiotype–Specific Suppressor T Cell with Antigen/Antibody Complexes", 157 J. Exp. Med. 1713 (1983).

Blaser et al, "Immune Networks in Immediate Type Allergic Diseases", 418 Ann. NY Acad.Sci. 330 (1983).

Blaser et al, "Regulation of the IgE Antibody Response by Idiotype–Anti–Idiotype Network", 32 Prog. Allergy 203 (1982).

Blaser et al, "Regulatory Effects of Isologous Anti–idiotypic Antibodies on the Formation of . . . ", 14 Eur. J. Immunol. 93–98 (1984) 50 Fed. Reg. 3082 (Jan. 23, 1985).

Fox, *Nature* 314, 1985, pp. 132–133.

Gene Cloning, 1984, ed. Glover, pp. 102–104.

Principles of Gene Manipulation, 1981, ed. Old et al., pp. 104–105, 119–120.

Brackmann, H. H. et al., "Massive Factor–VIII Infusion In Haemophiliac With Factor–VIII Inhibitor, High Responder", *The Lancet,* vol. 2, p. 933 (1977).

1

PHARMACEUTICAL COMPOSITION AND METHOD FOR THE SUPPRESSION OF FACTOR VIII INHIBITOR PRODUCTION

This application is a continuation of application Ser. No. 07/844,928, filed Mar. 4, 1992, now abandoned, which is a continuation of 07/255,350 filed Oct. 11, 1988, now abandoned, which is a continuation-in-part of 07/038,985 filed Apr. 16, 1987, now abandoned, which is a continuation-in-part of 06/651,073 filed Sep. 17, 1984, now U.S. Pat. No. 4,740,371.

BACKGROUND OF THE INVENTION

The present invention relates to pharmaceutical compositions containing complexes of factor VIII antigen and factor VIII inhibitor, and their use in suppressing the production of factor VIII inhibitor.

Blood coagulation factor VIII normally circulates at extremely low yet satisfactory concentrations in the blood plasma and plays a critical role in the blood coagulation process. Unsatisfactory levels of factor VIII cause delayed clotting of the blood and severe bleeding complications in persons suffering classical hemophilia, also known as hemophilia A. As a result, hemophiliacs fail to control hemorrhage even after minor injuries and suffer numerous associated maladies.

Hemophilia A has been treated for many years by administering dosages of commercially available factor VIII to raise the factor VIII concentration in the blood to normal levels. Usually, the treatment is quite effective and allows hemophiliacs to enjoy normal lives. Six to twenty percent of hemophiliacs have immune systems that generate inhibitor to factor VIII, however, and these individuals respond unsatisfactorily to conventional factor VIII treatment. This is especially true for about two-thirds of patients with inhibitors who are so-called "high responders." Injections of factor VIII into these individuals boost inhibitor levels to very high values.

Factor VIII inhibitor consists of alloantibodies against factor VIII. The antibodies are typically of the IgG class, and are only rarely of the IgM or IgA class. The inhibitor attacks and neutralizes the commercial supplement of factor VIII, rendering it ineffective in the blood coagulation process. Levels of inhibitor are measurable in Bethesda Units.

Bleeding complications associated with factor VIII inhibitor are not limited to hemophiliacs. Autoantibodies to factor VIII may arise in non-hemophiliac patients with rheumatoid arthritis, systemic lupus erythematosus, or drug hypersensitivity, in multiparous women, and even in apparently healthy elder individuals. Symptoms similar to those associated with hemophilia occur in these individuals.

Several treatments are known to counter the immunological response against factor VIII of hemophiliacs and others carrying factor VIII inhibitor, but these treatments have not been totally satisfactory. Treatment with very high doses of factor VIII alone has succeeded in a majority of patients but is typically prolonged and extremely expensive. Moderately high doses of factor VIII alone can be effective in a much lower proportion of patients and usually in patients with the lowest titres of inhibitors. Treatment with factor IX complex or so-called prothrombin complexes is difficult to evaluate in the absence of specific assay. The use of porcine factor VIII instead of human factor VIII is a temporary measure as it is highly immunogenic. Selected preparations of pooled gammaglobulins administered intravenously are effective in lowering the inhibitor levels, but only in some cases. Extracorporeal removal of inhibitors on protein A-Sepharose is cumbersome. A combination of extracorporeal removal of inhibitors with immunosuppressive drugs, intravenous gammaglobulins and factor VIII has recently shown success, but is considered hazardous for patients whose immune systems may be damaged for other reasons.

It is accordingly an object of the present invention to provide a pharmaceutical composition and method for effectively suppressing the production of factor VIII inhibitor.

It is a further object of the invention to provide a pharmaceutical composition and method for suppressing the production of factor VIII inhibitor that is safe, relatively inexpensive, and achieves the suppression in a relatively short period of time.

It is a further object of the invention to provide a pharmaceutical composition and method for substantially completely eliminating factor VIII inhibitor from the patient.

Other objects of the present invention will be apparent from the foregoing detailed description.

SUMMARY OF THE INVENTION

The present invention satisfies these objects by providing pharmaceutical compositions containing an immune complex comprising a factor VIII antigen component and a factor VIII inhibitor component, and a pharmacologically acceptable carrier or diluent. The antigen and inhibitor components are present in a ratio such that relevant binding sites of the antigen are blocked by the inhibitor, whereby the antigen produces essentially no detrimental immunologic reaction when administered to the patient. The compositions are administered to patients to suppress the production of factor VIII inhibitor.

DETAILED DESCRIPTION OF THE PREFERRED EMBODIMENTS

The present invention achieves numerous advantages over prior art treatments for controlling the occurrence of inhibitor to factor VIII. First and most fundamentally, the invention acts at the causative level, and in many cases arrests the body's production of inhibitor. Many patients show meaningful improvement after relatively short periods of treatment. The improvement progresses rapidly and the inhibitor is eventually completely eliminated in most cases.

Second, the invention requires only low dosages of factor VIII. Commercially prepared factor VIII is relatively expensive and the reduced requirements of the present invention allow cost savings over treatments in which high dosages of the factor are required. After the invention arrests inhibitor production, use of normal amounts of factor VIII in conventional therapy effectively controls hemophilia.

Third, the inventive composition by its nature causes little if any toxicity. The immune complex is preferably formed of components already present in the patient, or synthesized components that closely mimic the indigenous components. Other components of the composition are pharmacologically compatible and may otherwise be varied with considerable latitude to avoid any possible adverse reaction that might be specific to a particular individual. The simplicity and largely indigenous nature of the composition also allows treatment in accord with the present invention to be combined safely and effectively with prior art therapies as may be beneficial.

Fourth, the invention avoids other disadvantages of conventional treatments, yet yields comparable and usually superlative results. The invention, for example, requires no radical procedures as in the case of plasmapheresis, and does not suppress the body's immunologic defense to antigens unrelated to the disorder. Still other advantages of the invention will be readily apparent to those skilled in the art.

The specific mode of action by which the present invention achieves its success is unknown, but it is hypothesized that the benefits flow from the occurrence of factor VIII-factor VIII inhibitor immune complex that is inevitably present in the mixtures of factor VIII and inhibitor. It is believed that the immune complex stimulates the production of anti-idiotypic antibodies against the inhibitor. The anti-idiotypic antibodies in turn suppress the production of inhibitor at the cellular or possibly the humoral level. This hypothesis is offered to allow a better understanding of the invention, but is not to be construed in any way to limit the scope of the appended claims.

Human factor VIII has been isolated and purified and is commercially available as HEMOFIL M (Registered U.S. Patent and Trademark Office) from Hyland Division, Baxter Healthcare Corporation, Deerfield, Ill. Copending U.S. application Ser. No. 32,800, filed Mar. 31, 1987, describes a preferred method for preparing this antigen. Because the inhibitor will react only with factor VIII, almost any preparation of factor VIII is suitable, even factor VIII in the form of crude extracts, provided it is devoid of toxic substances. However, the use of pure or relatively pure preparations of factor VIII is preferred because it is then easier to assess and control the amount of factor VIII present, which is important in controlling doses.

Once the factor VIII has been obtained, the inhibitor is derived from three possible sources: (a) immunized animals, (b) individual blood donors and pooled plasma from multiple donors, and (c) the patient himself. It is preferred to use inhibitor from the patient in the sense that the patient will normally have larger amounts of the inhibitor than will blood donors. On the other hand, the use of inhibitor from pooled plasma is commercially desirable since it allows the preparation of pre-packaged immune complexes without involving the patient. Nevertheless, the degree of cross-reactivity of idiotypes present on inhibitor molecules from various individual plasma sources, as present in plasma pools, may be variable and may thus affect the efficacy of the treatment. Inhibitors of animal origin are generally the least desirable because of the risk of undesirable side reactions.

The inhibitor is polyclonal or monoclonal and is present in one embodiment in the form of an immunoglobulin fraction such as F(ab')$_2$. The use of polyclonal antibodies decreases the risk of antigenic reactions against unmasked antigenic determinants. A method for preparing monoclonal antibodies is described in "Immunochemical Techniques - Part 1 - Hybridoma Technology and Monoclonal Antibodies", *Methods in Enzymology*, Vol. 121, edited by J. J. Langone et al. and published in 1986 by Academic Press, Inc.

The inhibitor is preferably purified by various known techniques. Purification has the advantage of removing therapeutically irrelevant materials. One suitable purification technique involves specific adsorption on factor VIII which has been insolubilized by coupling to a solid phase. The inhibitor is then recovered by elution under conditions which dissociate the immune complex, such as conditions of extreme pH, or by the use of chaotropic agents. Because therapeutic preparations of factor VIII may contain small amounts of a larger protein known as von Willebrand factor, inhibitor prepared in this fashion may contain small amounts of antibodies against this associated protein, without consequence to the effectiveness of the invention.

Compositions of the invention are made by mixing the factor VIII with the inhibitor in a form suited to the particular mode of administration that is selected. Sufficient inhibitor must be used to block essentially all of the available binding sites of factor VIII to which the inhibitor is specific, so that there is practically no antigenic effect by factor VIII when the composition is administered. The minimum amount of inhibitor is normally a molar equivalent for reaction with factor VIII, and the inhibitor is preferably present in a molar excess. There is no maximum to the amount of inhibitor, but for safety, a molar excess of up to about 100 is used. An even larger inhibitor excess can be used but is wasteful of the valuable material. Thus, a suitable factor VIII to inhibitor molar ratio ranges from about 1:1 to 1:100, and preferably from at least about 1:3 to 1:100.

One simple method of preparing the mixture of factor VIII and inhibitor, which avoids the necessity of purifying the factor VIII or inhibitor, is the use of the immune precipitate. In one embodiment, the precipitate is prepared by incubating a crude preparation of immunoglobulin from the patient's plasma or serum with the factor VIII and then centrifuging. The precipitation process is enhanced by the addition of polymers such as polyethylene glycol and dextran, or biological reagents such as rheumatoid factor or the Clq factor of complement. These techniques are well known in the art.

The compositions of the invention contain other components in addition to factor VIII and inhibitor. In the case of injectables, suitable additional components include human albumin to prevent denaturation of the inhibitor, antiseptic agents such as phenol, and adjuvants such as peptidoglycans.

Suitable liquid carriers for the composition when in injectable form include distilled water, or more preferably saline or buffered saline. In preferred embodiments, the composition includes a saline carrier of 9 grams per liter of sodium chloride, or a buffered saline carrier having a pH of 7.4. Suitable liquid carriers are of low irritance, e.g., of neutral pH and physiological ionic strength. The selection of other pharmacologically acceptable carriers and diluents for use in the compositions is within the skill of those ordinarily skilled in the art.

The compositions of the invention are prepared in a variety of forms depending on the manner of administration. They are suitably prepared in a sterile injectable form, slow-release implant form, or as protected enteric capsules or the like. Other suitable forms will be readily apparent to those ordinarily skilled in the art.

When the compositions are prepared in liquid form, the liquids are suitably solutions or suspensions. The liquids are stored in ampules or are lyophilized and reconstituted immediately prior to use. The compositions of the invention are fairly stable, and in sterile ampules, can normally be stored at 4° C. for a limited time, or at −20° C. for longer periods. Since factor VIII is highly susceptible to proteolytic digestion, the addition of a proteolytic inhibitor can markedly increase storage life. Lyophilization also increases storage life.

The injectable compositions of the invention are injected intradermally, subcutaneously, intramuscularly, and intravenously. The intradermal route is preferred because it provides a suitable way of presenting the compositions to the immune system of the patient being treated. The frequency of injections varies very widely, for example, from several daily to yearly, depending upon the severity of the disease and the stage of treatment.

The strength of the compositions is preferably expressed in terms of the factor VIII concentration and the factor VIII to inhibitor ratio. A suitable dosage range for the factor VIII antigen component of the compositions is from about one international factor VIII unit per kilogram of body weight, up to about 100 units per kilogram, and the factor VIII to inhibitor ratio is selected to mask the appropriate immunogenic sites of factor VIII. Dosages of from about 1 nanogram to 10 micrograms are suitable. The initial factor VIII dosage is preferably relatively small and is then increased as necessary to a level at which the production of inhibitor is sufficiently suppressed. Thus, a suitable regimen calls for an initial intradermal dose of one international factor VIII unit per kilogram, followed one week later by a second dose of 10 units per kilogram. Additional weekly doses are administered as necessary, and are increased progressively to 100 units per kilogram if required for suppression of factor VIII inhibitor formation.

It will be readily apparent to those skilled in the art that modifications to the presently described techniques of preparation may be appropriate in the practice of the present invention and are within the scope of the invention as claimed. In order that the invention may be more fully understood, the following examples illustrate how it is made and used.

Example 1

HEMOFIL M (Registered U.S. Patent and Trademark Office) commercially available from Baxter Hyland Division, Glendale, Calif., is used as the factor VIII antigen component. The antigen is purified by gel filtration chromatography on Ultrogel AcA 44 and/or Ultrogel AcA 54 (LKB) and, in some cases, by specific immunoadsorption on insolubilized polyclonal or monoclonal specific antibodies.

The antigen is then coupled with carbodiimide to carboxylated agarose (CH-Sepharose 4B; Pharmacia Fine Chemicals). For this purpose, the antigen is incubated at pH 4.5 with 0.1M carbodiimide and carboxylated agarose for 24 hours at 21° C.

The remaining reactive groups on the solid phase are inactivated by its incubation with 1M glycine for 3 hours at 21° C. The immunoadsorbent is then washed alternatively with 0.1M acetate buffer pH 4.0 and 0.1M carbonate buffer pH 8.3, both containing 0.5M NACl. To avoid the elution of undesired material with the antibodies of interest, the gel is submitted prior to immunoadsorption to the elution conditions to be described hereafter and to an additional washing with 3M ammonium thiocyanate.

The factor VIII inhibitor component is prepared from patient plasma as follows. The immunoglobulin fractions (1–2 g) from each of the patients are applied onto an immunoadsorbent column (5 ml; 10×2 cm; flow rate 20 ml/h) and the specific inhibitor antibodies are recovered after appropriate washings. Washing is accomplished by:

1. Washing with PBS until the optical density at 280 mm is less than 0.02.

2. Washing with PBS containing 1M NaCl to eliminate non-specific adsorption.

3. Washing with 50 ml of 9 g/l NaCl.

4. Eluting with successive aliquots of 50 ml citric acid, pH 2.7, followed by PBS.

Each new wash and elution step is pursued until no protein is detectable in the effluent. Fractions eluted with citric acid and PBS are pooled immediately, neutralized with drop-wise addition of 2M TRIS-HCl buffer, concentrated on a YM 10 ultrafiltration membrane and dialyzed against PBS for 48 hours. The eluate is then filtered through a 0.22 micron filter and stored at 4° C. in sterile vials. The immunoadsorbent is washed with 3M ammonium thiocyanate for 20 minutes and finally with 100 ml PBS. All buffers are filtered in a 0.22 micron filter.

The neutralizing capacity of the inhibitor is determined by its ability to neutralize the clot-promoting activity of factor VIII. HEMOFIL M (Registered U.S. Patent and Trademark Office) and patient-derived antibody complexes are constructed using the so-derived neutralizing capacity information, with a weight ratio of antigen to antibody of 1:3.

The antigen and inhibitor are mixed in 9 g/l NaCl containing 0.3 percent human serum albumin and 0.4 percent phenol. All solutions are passed through a sterile 0.22 micron filter and handled in sterile conditions. The final volume is 2 ml and contains 300 micrograms inhibitor and 100 micrograms antigen. The injectable solutions so prepared are kept in sealed vials at 4° C. until used.

Example 2

The composition is prepared in accordance with Example 1 except that the mixture contains 10 micrograms antigen and the ratio of antigen to inhibitor is 1:3.

Example 3

The composition is prepared in accordance with Example 1 except that the mixture contains 1 microgram antigen and the ratio of antigen to inhibitor is 1:30.

Example 4

The composition is prepared in accordance with Example 1 except that the mixture contains 0.1 microgram antigen and the ratio of antigen to inhibitor is 1:10.

Example 5

The composition is prepared in accordance with Example 1 except that the mixture contains 0.01 microgram antigen and the ratio of antigen to inhibitor is 1:3.

Example 6

The composition is prepared in accordance with Example 1 except that the mixture contains 1000 nanograms antigen and the ratio of antigen to inhibitor is 1:1.

Example 7

The composition is prepared in accordance with Example 1 except that the mixture contains 100 nanograms antigen and the ratio of antigen to inhibitor is 1:60.

Example 8

The composition is prepared in accordance with Example 1 except that the mixture contains 10 nanograms antigen and the ratio of antigen to inhibitor is 1:80.

Example 9

The composition is prepared in accordance with Example 1 except that the mixture contains 1 nanogram antigen and the ratio of antigen to inhibitor is 1:100.

Example 10

The composition is prepared in accordance with Example 1 except that the mixture contains 50 nanograms antigen and the ratio of antigen to inhibitor is 1:20.

Example 11

The composition is prepared in accordance with Example 1 except that the mixture contains 10 micrograms antigen and the ratio of antigen to inhibitor is 1:40.

Example 12

The composition is prepared in accordance with Example 1 except that the mixture contains 500 nanograms antigen and the ratio of antigen to inhibitor is 1:5.

Example 13

The immunoadsorbent is prepared as described in Example 1, but the factor VIII antigen is in the form of factor VIII fragments generated by proteolytic cleavage of factor VIII, as taught in Eaton, Rodriguez, and Vehar, "Proteolytic Processing of Human Factor VIII," *Biochemistry*, 25, pp. 505–512 (1986). Antibody is prepared from pooled normal plasma (at least 10 donors in the pool). The neutralizing capacity is determined and the complexes are constructed and formulated as described in Example 2.

Example 14

The immunoadsorbent is prepared as described in Example 1, but the inhibitor is Gammagard (Baxter Hyland Division, Glendale, Calif.). The neutralizing capacity is determined and the complexes are constructed and formulated as described in Example 3.

Example 15

The antibody is prepared as described in Example 10, but the complexes are constructed using factor VIII antigen produced by recombinant DNA technology in accordance with the teachings of Toole et al., *Nature*, 312, 342–348 (1984).

Example 16

Antigen-antibody complexes are constructed as described in Example 12, but using HEMOFIL M (Registered U.S. Patent and Trademark Office) and mouse monoclonal antibody directed against factor VIII, the antibody being prepared as taught in U.S. patent application 32,800, filed Mar. 31, 1987. The mouse monoclonal antibody is the antibody used to purify HEMOFIL M (Registered U.S. Patent and Trademark Office). Monoclonal antibodies from other mammalian species including human may also be used.

Example 17

Antigen-antibody complexes are constructed as described in Example 1, but the a ntigen is synthetically prepared by organic synthetic techniques, using amino acid sequences revealed in Toole et al., *Nature*, 312, pp. 342–348 (1984), and then combined with F(ab)$'_2$ antibody fragments prepared by standard techniques.

Example 18

Complexes prepared as described in the above examples are injected intradermally into hemophilia A patients with anti-factor VIII antibody. In each case, the first dose contains an amount of factor VIII antigen component equivalent to 1 international unit of factor VIII per kilogram of patient body weight. A second dose, given one week later, contains an amount of factor VIII antigen component equivalent to 10 international units of factor VIII per kilogram of patient body weight. One week after this second injection, the patients' plasma contains no detectable anti-factor VIII antibody, the response to intravenously infused factor VIII is that normally expected in a hemophiliac, and the patients are treated thereafter on demand with factor VIII.

Example 19

Initial treatment of the patient is as described in Example 18. One week after the second injection, the patient's plasma still contains anti-factor VIII antibody. Complexes containing 20 international unit equivalents of factor VIII per kilogram of patient body weight are injected intradermally. In similar fashion, in subsequent weeks, complexes containing increasing dosages (30, 40, 50, etc. international units) of factor VIII are administered intradermally when anti-factor VIII antibody is still detectable in the patient's plasma. The highest dose used is 100 international unit equivalents per kilogram of patient body weight. When anti-factor VIII antibody is no longer detectable in the patient's plasma, intravenous factor VIII therapy on demand is commenced as described in Example 18.

Example 20

Treatment with antigen-antibody complex is carried out as described in Example 19. However, on first intravenous infusion treatment with factor VIII, it is determined that half-life and/or recovery of infused factor VIII is less than expected in a patient with hemophilia A. The patient is then treated with intravenous factor VIII, 200 units per kilogram, daily until the response to infusion is satisfactory. Subsequently, the patient is treated prophylactically with 50 units per kilogram, intravenously two or three times a week, as the clinical response dictates.

Example 21

A patient without previous factor VIII deficiency, who now has a bleeding disease caused by autoantibody to factor VIII, is treated according to the pattern described in Examples 18, 19 and 20. Ordinarily these patients respond to such treatment more readily than hemophiliacs, and prophylactic factor VIII maintenance therapy as described in Example 20 is rarely if ever required.

Example 22

A complex prepared as described in the above examples is injected intradermally in doses containing an amount of factor VIII antigen component equivalent to 100 international units of factor VIII per kilogram of the patient's body weight. A dose is administered twice daily. Twenty doses are administered in total.

Example 23

A complex prepared as described in the above examples is injected intradermally in doses containing an amount of factor VIII antigen component equivalent to 20 international units of factor VIII per kilogram of the patient's body weight. A dose is administered three times daily. Fifteen doses are administered in total.

Example 24

A complex prepared as described in the above examples is injected intradermally in doses containing an amount of factor VIII antigen component equivalent to 80 international units of factor VIII per kilogram of the patient's body weight. A dose is administered once daily. Ten doses are administered in total.

Example 25

A complex prepared as described in the above examples is injected intradermally in doses containing an amount of factor VIII antigen component equivalent to 60 international units of factor VIII per kilogram of the patient's body weight. A dose is administered monthly. Four doses are administered in total.

Example 26

A complex prepared as described in the above examples is injected intradermally in a dose containing an amount of factor VIII antigen component equivalent to 40 international units of factor VIII per kilogram of the patient's body weight. Only one dose is administered.

Example 27

A complex prepared as described in the above examples is injected intradermally in doses containing an amount of factor VIII antigen component equivalent to 50 international units of factor VIII per kilogram of the patient's body weight. A dose is administered tri-monthly. Two doses are administered in total.

Example 28

A complex prepared as described in the above examples is injected intradermally in doses containing an amount of factor VIII antigen component equivalent to 50 international units of factor VIII per kilogram of the patient's body weight. A dose is administered annually. Five doses are administered in total.

Example 29

Treatment proceeds as described in the preceding examples, but is supplemented with intravenous immune globulin in ways known to those skilled in the art, as taught in Nilsson et al., *N. Eng. J. Med.*, 318, pp. 947–950 (1988).

Example 30

Treatment proceeds as described in the preceding examples, but is supplemented by conventional treatment with cyclophosphamide as taught in the Nilsson et al. reference.

Example 31

Treatment proceeds as described in the preceding examples, but is supplemented with both intravenous immune globulin and cyclophosphamide.

The foregoing examples describe a number of methods for respectively preparing the antigen and inhibitor components, and these and other methods are employed in various combinations to achieve the inventive compositions. It is envisaged that the factor VIII antigen component may suitably be produced by: (1) "classical" concentration from a human plasma pool, (2) purification by immunoadsorption from a human plasma pool, (3) genetic engineering, (4) peptides or small protein fragments derived from factor VIII preparations made from methods (1) to (3) above, and (5) peptides prepared synthetically. One of these methods for producing the antigen component may suitably be combined with any one of the following forms envisaged for the inhibitor component: (1) purified inhibitor from the individual donor's plasma, (2) purified inhibitor from a pool of plasma, (3) F(ab)'$_2$ fragments of purified preparations, (4) monoclonal antibodies, and (5) "chimeric" antibodies, i.e., "combination" antibodies with the binding site derived from animal sources and the framework derived from human sources. As used in the appended claims, factor VIII antigen component refers to factor VIII molecules or fragments, regardless of the manner in which they are prepared, that comprise factor VIII antigenic determinants. Factor VIII inhibitor component, as used in the claims, refers to antibodies and fragments, regardless how prepared, that comprise the immunogenic binding sites for factor VIII.

Having illustrated the practice of the invention in connection with several specific embodiments, those of ordinary skill in the art are taught to vary the elements of the invention, such as factor VIII dosage, factor VIII to inhibitor ratio, carrier or diluent, additives, and manner and periodicity of administration as may be appropriate to suppress factor VIII inhibitor production. It will be readily apparent to those skilled in the art that these and other modifications are within the spirit and scope of the present invention.

We claim:

1. A pharmaceutical composition suitable for administration to human beings for suppressing factor VIII inhibitor production in the treatment of hemophilia, said composition consisting essentially of:

an immune complex comprising factor VIII antigen component and factor VIII inhibitor component, said factor VIII inhibitor component being at least partly human, and said components being present in a ratio such that said inhibitor component neutralizes said antigen component; and a pharmacologically acceptable carrier or diluent.

2. The composition of claim 1 wherein said antigen component is factor VIII prepared from human plasma.

3. The composition of claim 1 wherein said antigen component is factor VIII prepared by recombinant DNA technology.

4. The composition of claim 1 wherein said antigen component comprises factor VIII fragments.

5. The composition of claim 1 wherein said inhibitor component is antibody derived from a single patient.

6. The composition of claim 1 wherein said inhibitor component is antibody derived from pooled plasma of multiple donors.

7. The composition of claim 1 wherein said inhibitor component is F(ab)'$_2$ antibody fragment.

8. The composition of claim 1 wherein said inhibitor is chimeric antibody.

9. The composition of claim 1 wherein said inhibitor component is present, relative to said factor VIII component, in a molar excess.

10. The composition of claim 1 wherein the antigen component to inhibitor component molar ratio is from about 1:1 to about 1:100.

11. The composition of claim 10 wherein said ratio is at least about 1:3.

12. The composition of claim 1 wherein the antigen component is present in a dose of from about 1 to 100 international units per kilogram of body weight.

13. The composition of claim 1 wherein said carrier or diluent is of approximately neutral pH.

14. The composition of claim 1, wherein said immune complex is formed in vitro.

15. A method for suppressing the factor VIII inhibitor production of a patient suffering hemophilia who has been administered factor VIII and whose treatment has been complicated by the presence of factor VIII inhibitor, comprising the steps of:

preparing a pharmaceutical composition suitable for administration to human beings that comprises an effective amount of an immune complex of factor VIII antigen component and factor VIII inhibitor component, said factor VIII inhibitor component being at least partly human, said components being present in a ratio such that said inhibitor component neutralizes said antigen component, and a pharmacologically acceptable carrier or diluent; and parenterally administering said composition to said patient.

16. The method of claim 15 further comprising the step of preparing said antigen component by recombinant DNA technology.

17. The method of claim 15 further comprising the step of preparing said antigen component by proteolytic cleavage of factor VIII molecules.

18. The method of claim 15 further comprising the step of preparing said antigen synthetically.

19. The method of claim 15 further comprising the step of deriving anti-factor VIII antibodies from a pooled plasma of multiple donors for use as said inhibitor component.

20. The method of claim 15 further comprising the step of preparing said inhibitor in the form of F(ab)'$_2$ fragment.

21. The method of claim 15 further comprising the step of preparing said inhibitor in the form of chimeric antibody.

22. The method of claim 15 further comprising the step of selecting an amount of said antigen component ranging from 1 to 100 international units per kilogram of said patient's body weight.

23. The method of claim 15, wherein the composition is administered intradermally.

24. The method of claim 15, wherein the composition is administered subcutaneously.

25. The method of claim 15, wherein the composition is administered intramuscularly.

26. A method for suppressing the factor VIII inhibitor production of a patient suffering hemophilia who has been administered factor VIII and whose treatment has been complicated by the presence of factor VIII inhibitor, comprising the steps of:

preparing a pharmaceutical composition suitable for administration to human beings that comprises an effective amount of an immune complex of factor VIII antigen component and factor VIII inhibitor component, said factor VIII inhibitor component being at least partly human, said components being present in a ratio such that said inhibitor component neutralizes said antigen component, and a pharmacologically acceptable carrier or diluent;

parentally administering said composition to said patient; and deriving anti-factor VIII antibodies from said patient for use as said inhibitor component.

* * * * *